United States Patent
Ueno et al.

(10) Patent No.: US 8,660,336 B2
(45) Date of Patent: Feb. 25, 2014

(54) DEFECT INSPECTION SYSTEM

(75) Inventors: Taketo Ueno, Fujisawa (JP); Yasuhiro Yoshitake, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/593,227

(22) Filed: Aug. 23, 2012

(65) Prior Publication Data
US 2013/0058558 A1 Mar. 7, 2013

Related U.S. Application Data

(63) Continuation of application No. 12/957,018, filed on Nov. 30, 2010, now Pat. No. 8,275,189, which is a continuation of application No. 11/501,815, filed on Aug. 10, 2006, now Pat. No. 7,881,520.

(30) Foreign Application Priority Data

Sep. 7, 2005 (JP) .................. 2005-258664

(51) Int. Cl.
G06K 9/00 (2006.01)
G01R 31/26 (2006.01)
G01N 21/00 (2006.01)
G06F 17/50 (2006.01)

(52) U.S. Cl.
USPC ............. 382/149; 356/237.1; 716/51; 438/16

(58) Field of Classification Search
USPC .................. 382/144, 149; 356/237.1; 716/51; 438/16
See application file for complete search history.

(56) References Cited

U.S. PATENT DOCUMENTS

| | | | | |
|---|---|---|---|---|
| 5,943,437 A | * | 8/1999 | Sumie et al. ................. | 382/149 |
| 6,759,655 B2 | * | 7/2004 | Nara et al. ................... | 850/9 |
| 7,142,294 B2 | * | 11/2006 | Shibata et al. .............. | 356/237.2 |
| 7,292,327 B2 | | 11/2007 | Nara et al. | |
| 7,508,973 B2 | * | 3/2009 | Okabe et al. ................. | 382/145 |
| 7,532,328 B2 | * | 5/2009 | Nara et al. .................... | 356/394 |
| 7,599,054 B2 | * | 10/2009 | Takeda et al. ............... | 356/237.5 |

(Continued)

FOREIGN PATENT DOCUMENTS

| | | |
|---|---|---|
| JP | 9-26396 | 1/1997 |
| JP | 2002-277404 | 9/2002 |

(Continued)

OTHER PUBLICATIONS

Official Action issued in Japanese Patent Application No. 2005-258664 on Mar. 16, 2010.

(Continued)

*Primary Examiner* — Kathleen Y Dulaney
(74) *Attorney, Agent, or Firm* — Antonelli, Terry, Stout & Kraus, LLP.

(57) ABSTRACT

A defect inspection system is disclosed for easily setting inspection conditions and providing an inspection condition and a defect signal intensity to an operator. The defect inspection system digitizes a defective image, and a reference image corresponding thereto and a mismatched portion of the defective image and the reference image as a defect signal intensity and accumulates them in association with the inspection condition. The inspection conditions are changed to repeat evaluations while repeating accumulating works until the evaluation of all the inspection conditions in a set range is completed. A recipe file including the accumulated conditions having the high defect signal intensity and an inspection condition item distribution as a inspection condition recipe is automatically outputted and provided to the operator.

16 Claims, 17 Drawing Sheets

(56) References Cited

U.S. PATENT DOCUMENTS

| | | | |
|---|---|---|---|
| 2001/0033683 A1* | 10/2001 | Tanaka et al. | 382/149 |
| 2002/0109088 A1* | 8/2002 | Nara et al. | 250/306 |
| 2003/0133027 A1* | 7/2003 | Itoh | 348/246 |
| 2004/0227079 A1* | 11/2004 | Nara et al. | 250/310 |
| 2004/0228515 A1* | 11/2004 | Okabe et al. | 382/145 |
| 2004/0243320 A1* | 12/2004 | Chang et al. | 702/30 |
| 2005/0060104 A1* | 3/2005 | Strader | 702/30 |
| 2006/0100730 A1* | 5/2006 | Parkes et al. | 700/108 |
| 2006/0236294 A1* | 10/2006 | Saidin et al. | 716/19 |
| 2009/0141264 A1 | 6/2009 | Shibata et al. | |

FOREIGN PATENT DOCUMENTS

| | | |
|---|---|---|
| JP | 2002-303586 | 10/2002 |
| JP | 2005-17159 | 1/2005 |
| JP | 2005-44912 | 2/2005 |
| JP | 2005-55447 | 3/2005 |

OTHER PUBLICATIONS

Office Action issued in Japanese Patent Application No. 2005-258664 on Oct. 26, 2010.

* cited by examiner

DEFECT INSPECTION SYSTEM

CROSS-REFERENCE TO RELATED APPLICATION

This application is a continuation of application Ser. No. 12/957,018, filed on Nov. 30, 2012, which is a continuation of application Ser. No. 11/501,815, filed on Aug. 10, 2006, now allowed, which claims the benefit of Japanese patent application No. JP 2005-258664 filed on Sep. 7, 2005, the disclosures of which are incorporated herein by reference.

BACKGROUND OF THE INVENTION

The present invention relates to a inspection technique of comparing an inspection image of an object to be inspected obtained by using light, electron beam, or the like and a reference image corresponding thereto and of detecting a defect such as a fine pattern defect or a foreign material occurring on a substrate from a difference between the images and, in particular, to a technique effectively applied to a defect inspection system for performing appearance inspection of a substrate for a semiconductor wafer, a photomask, a liquid crystal, or the like.

For example, in a defect inspection apparatus constituting the defect inspection system, a plurality of inspection condition items are present and the number of combinations thereof is tens or more. Therefore, prior to inspection, work (condition selecting work) is required for performing an inspection on some inspection conditions and selecting one condition that has the highest sensitivity of defect detection from the inspected conditions. However, there is such a problem that considerable skill is required to the work because of taking some of trial and error and further heavy workload is required.

As a method for solving the above problem, for example, techniques disclosed in Japanese Patent Laid-open Publication No. 2002-303586 and Japanese Patent No. 3300830 are known. The technique disclosed in Japanese Patent Laid-open Publication No. 2002-303586 allows even an unskilled person to set an inspection condition having high sensitivity of defect detection easily and in a short period of time by: inspecting an object to be inspected on a plurality of test conditions constituted from a plurality of inspection condition items set in advance while automatically changing inspection conditions; quantitatively arranging and displaying images, contrasts, luminance distributions, and the like on respective test conditions; performing automatic defect/misinformation discrimination based on the test inspection result; displaying the classification result on a map, and selecting the condition having a low misinformation ratio.

The technique disclosed in Japanese Patent No. 3300830 provides a method of comparing information about a defect detected on a defect inspection apparatus with data extracted from distribution of scattering light from a defect obtained according to simulation to classify the detected defects according to sizes and shapes, thereby making it possible to detect presence or absence of a defect such as a foreign material on a substrate, on a surface of which a pattern is formed, and further detect the size or shape of the defect rapidly and easily if the defect is present.

However, in the technique disclosed in Japanese Patent Laid-open Publication No. 2002-303586, a whole wafer is inspected while changing the inspection conditions and defect maps are arranged and displayed for the respective conditions, so that it is necessary to inspect the entire wafer by the number of inspection conditions. For example, when the technique is applied to an inspection apparatus whose throughput is not high, there is such a problem that an unrealistically long prior evaluation time is necessary. In addition, a sample that is an object to be inspected is required for setting an inspection condition.

Also, the technique disclosed in Japanese Patent No. 3300830 provides a method for classifying the simulation results according to the sizes and shapes of the defects. The method is useful for classifying the defects, but does not assist in setting of the inspection condition.

SUMMARY OF THE INVENTION

An object of the present invention is to provide a defect inspection system which can perform inspection condition setting easily and in a relatively short period of time, make an examination of the inspection condition setting even if there is no sample, and further provide an inspection condition and a defect signal intensity to a person, who sets an inspection condition, to assist in the inspection condition setting.

Outlines of representative ones of the inventions disclosed in the present application will be briefly described as follows.

The present invention is configured as a system comprising means having the following respective functions, for the purpose of semi-automation of condition setting of a defect inspection system which detects a defect by comparing an inspection image of an object to be inspected and a reference image: (1) a function of accumulating the inspection image and the reference image in association with the inspection condition; (2) a function of digitalizing, as a defect signal intensity, a mismatched portion of the inspection image and the reference image of the item (1) to accumulate the defect signal intensity in association with the inspection condition; (3) a function of changing the inspection conditions to repeat the accumulating works of the items (1) and (2) until evaluation on all the inspection conditions in a set range is completed; (4) a function of repeating the items (1) to (3) by the number of kinds of defects when a plurality of defects to be inspected are present; and (5) a function of automatically outputting, as an inspection condition recipe, a recipe file including the accumulated conditions having the high defect signal intensity and an inspection condition item distribution or of expressly providing the recipe file to a worker who performs the inspection condition setting.

Effects obtained from representative ones of the inventions disclosed in the present application will be briefly described as follows.

According to the present invention, in the condition setting of the defect inspection system which detects the defect by comparing the inspection image of the object to be inspected and the reference image, the inspection condition setting can be performed easily and in a relatively short period of time. It is possible to examine the inspection condition setting even when there is no sample. Further, the present invention provides a function capable of providing the inspection conditions and the defect signal intensities to a person, who sets the inspection condition, to assist in the inspection condition setting.

Those and other objects, features, and advantages of the invention will be apparent from the following more particular description of preferred embodiments of the invention, as illustrated in the accompanying drawings.

DESCRIPTION OF THE PREFERRED EMBODIMENTS

Figure 1:
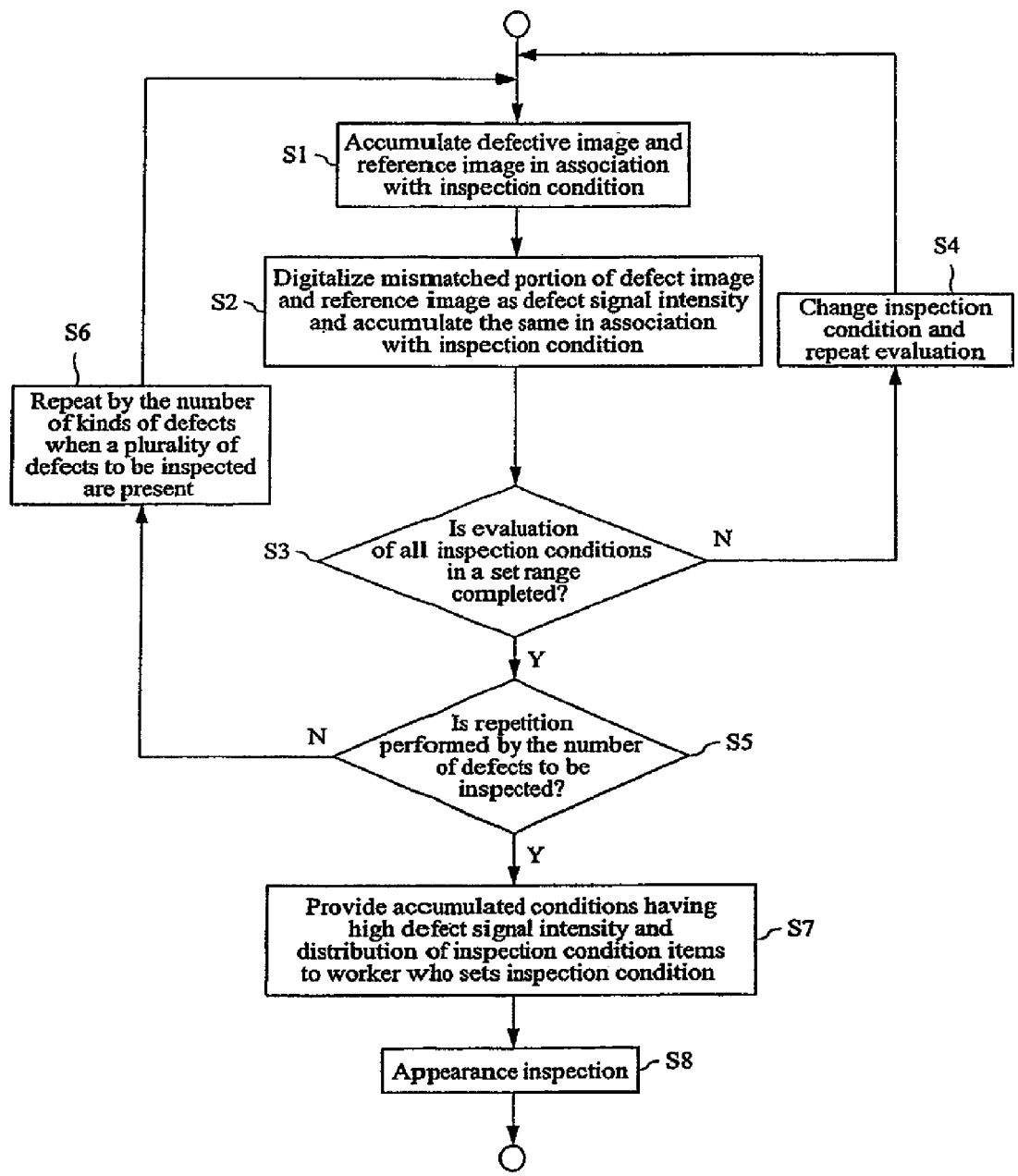
FIG. 1 is a diagram for explaining a concept of an operation flow of a defect inspection system in an embodiment of the present invention.

Embodiments of the present invention will be explained below in detail with reference to the drawings. Incidentally, throughout all figures for explaining the embodiments, the same reference numerals are in principle denoted by the same members and repetitive explanation thereof is omitted.

Concept of Embodiments of the Invention

Concept of embodiments of the present invention will be explained with reference to FIG. 1. FIG. 1 is a diagram for explaining a concept of an operation flow of a defect inspection system.

A defect inspection system according to the embodiments of the present invention has functions of performing the following operations.

In operations of the defect inspection system according to the embodiments of the present invention, as shown in FIG. 1, an image (called also "defective image") including a defect and its vicinity, which is an inspection image, and a reference image are first accumulated in association with an inspection condition (S1). Further, a mismatched portion of the defective image and the reference image is digitalized as a defect signal intensity and is accumulated in association with the inspection condition (S2). Whether evaluation of all the inspection conditions in a set range is completed is determined (S3), and the evaluation is repeated while changing the inspection conditions and repeating the accumulating works of S1 and S2 until all the evaluations are completed (S4). When a result of determination at S3 indicates that all the evaluations have been completed, whether the repeat is performed by the number of defects to be inspected is determined (S5). When the result of the determination at S5 indicates that there are a plurality of defects to be inspected, the works at S1 to S4 are repeated by the number of kinds of the defects (S6). When there are not a plurality of defects to be inspected, a recipe file including an accumulated condition having a high defect signal intensity and an inspection condition item distribution is automatically outputted as an inspection condition recipe to expressly provide the same to a worker who sets the inspection condition (S7). Appearance inspection of detecting a pattern defect or a foreign material on a substrate is performed (58). The appearance inspection is performed to a semiconductor wafer, a photomask, a liquid crystal, or the like.

Also, in the defect inspection system according to the embodiments of the present invention, when the defective image and the reference image are acquired, there are the following methods as detailed below: (1) a method for using an inspection apparatus which can specify coordinates of a defect present on a substrate in setting an inspection condition, can load an inspection condition recipe file produced in the outside, has a function of outputting a defective image and its reference image when the coordinates of the defect is specified on the recipe, and obtain, as a defective image and its reference image, images outputted by the inspection apparatus; and (2) a method for producing a simulation model based on a structural drawing of a substrate to be inspected, calculating the case where a defect is present and the case where no defect is present according to simulation based on a defect inspection method using a means for realizing the operations shown in FIG. 1, and obtaining the defective image and its reference image.

Further, when the mismatched portion of the inspection image and the reference image is digitalized as a defect signal intensity, there are the following methods as detailed later: (1) a method for using a difference image between the inspection image and its reference image; (2) a method for using an indicator of defect determination in an inspection apparatus having a means for realizing the operations shown in FIG. 1; (3) a method for using an inspection apparatus which can specify coordinates of a defect existing on the substrate in setting the inspection condition, can load an inspection condition recipe file produced in the outside, has a function of outputting a defect determination image when the coordinates of a defect is specified on the recipe, and define brightness of the image outputted by the inspection apparatus as a defect signal intensity.

Each embodiment based on the concept of the embodiments of the present invention will be detailed below.

First Embodiment

Figure 2:
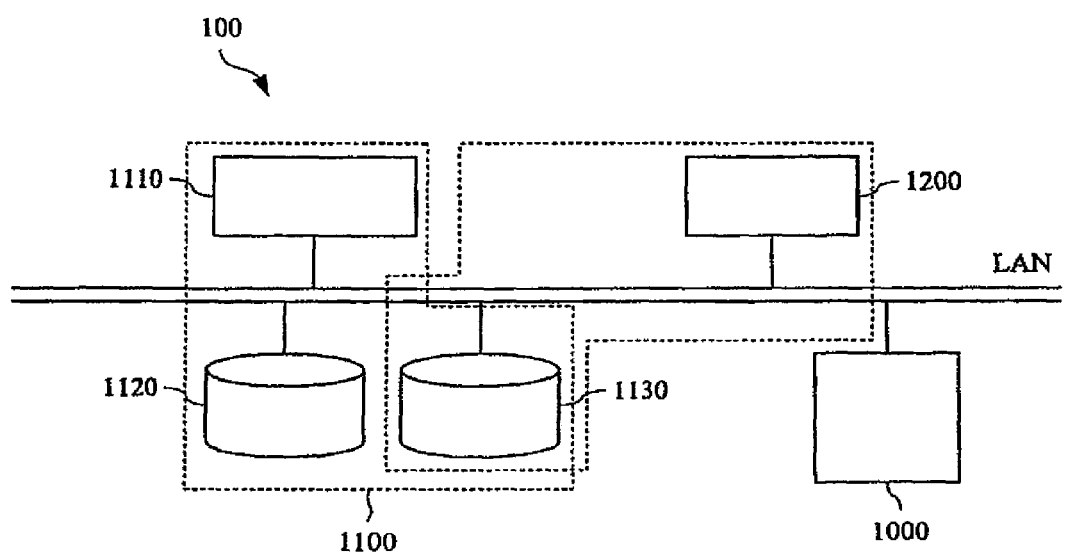
FIG. 2 is a diagram for explaining one example of a configuration of a defect inspection system in a first embodiment of the present invention.
Figure 3:
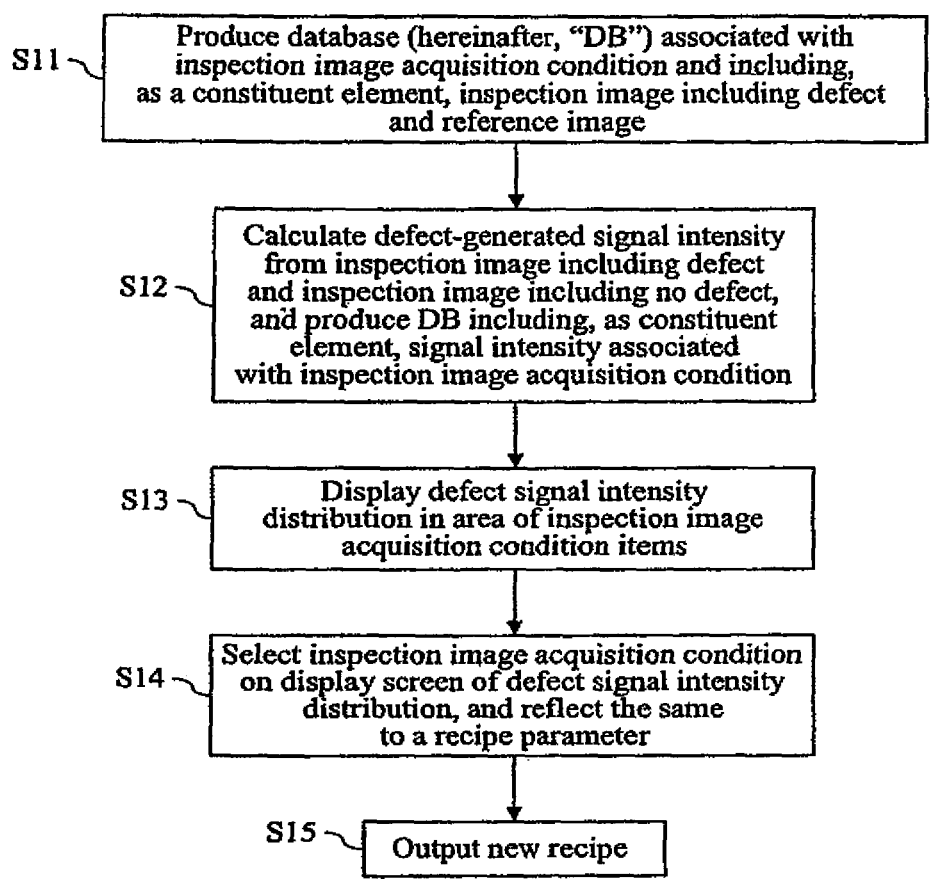
FIG. 3 is a diagram for explaining one example of outline of operation logic of the defect inspection system in the first embodiment of the present invention.
Figure 4:
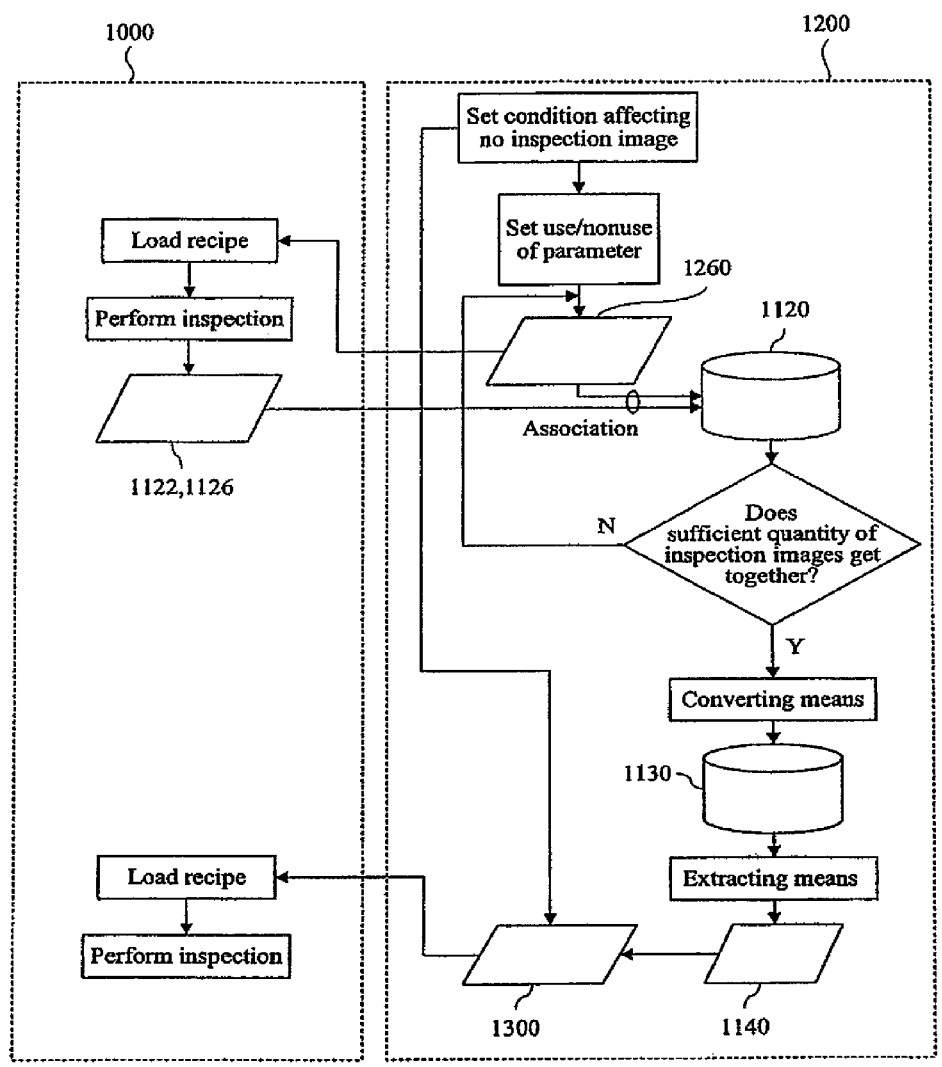
FIG. 4 is a diagram for explaining one example of an operation flow of the defect inspection system in the first embodiment of the present invention.
Figure 5:
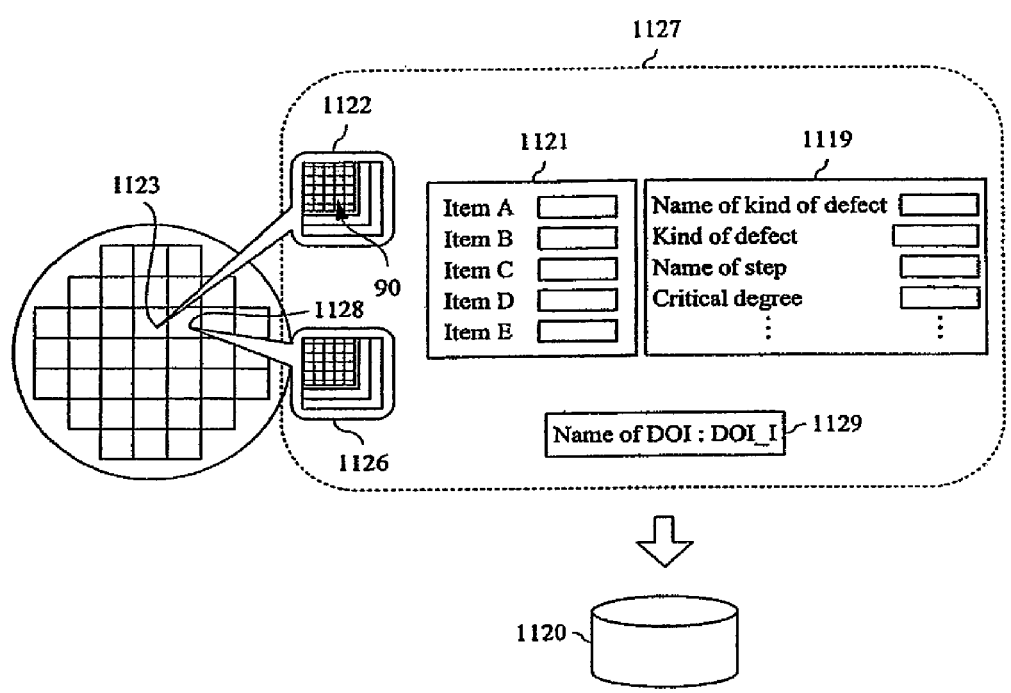
FIG. 5 is a diagram for explaining constituent elements of an image DB and one example of a DB producing method in the defect inspection system in the first embodiment of the present invention.
Figure 6:
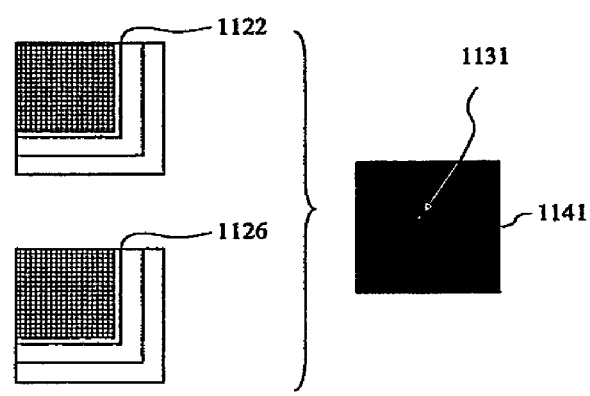
FIG. 6 is a diagram for explaining one example of defect information comprising an image including a defect, a reference image, and a defect signal image produced from the both images in the first embodiment of the present invention.
Figure 7A:
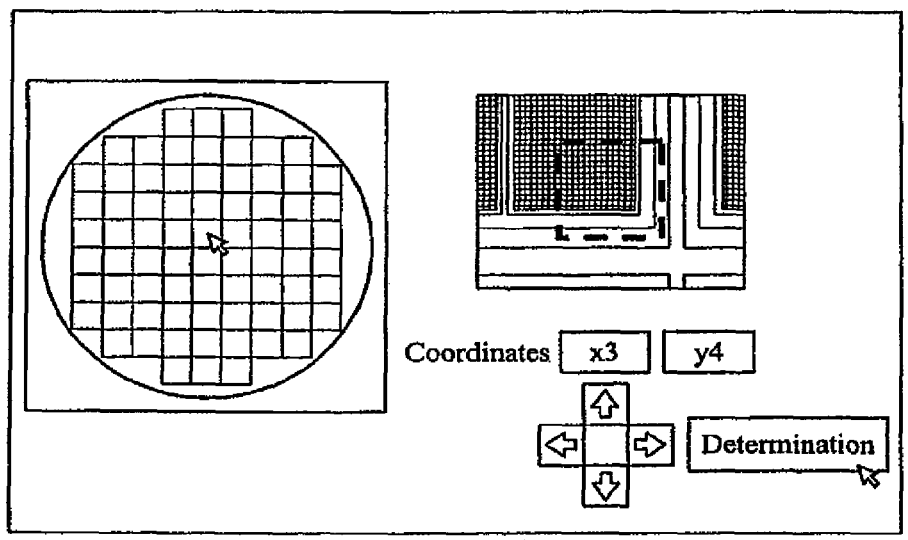
FIG. 7A is a diagram for explaining a defect-coordinate specifying assistance screen in the first embodiment of the present invention and for showing a wafer map, a review image, and a coordinate inputting portion where coordinates on the review image are inputted.
Figure 7B:
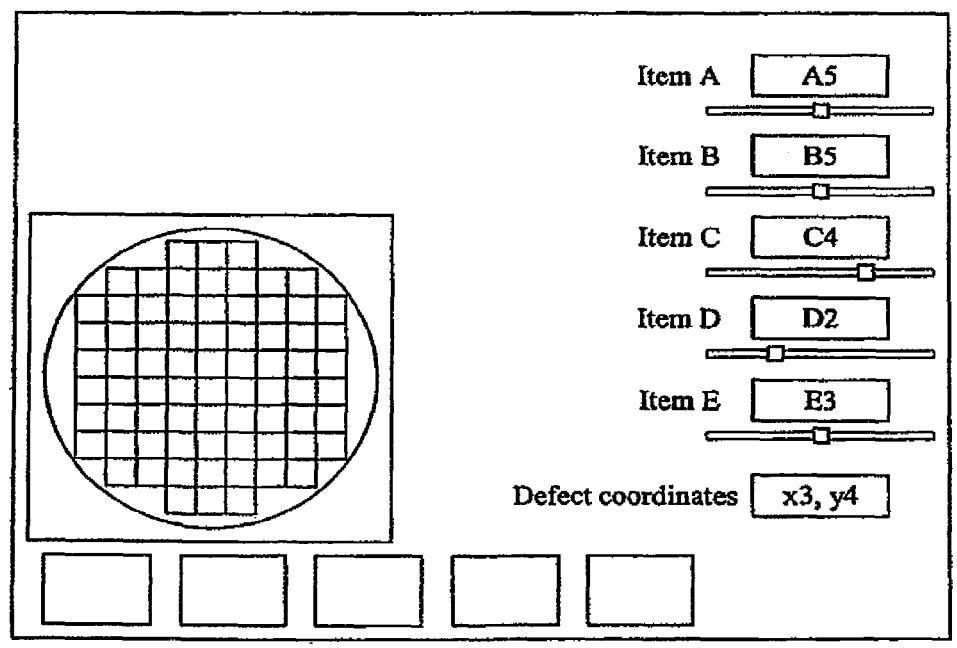
FIG. 7B is a diagram for explaining a defect-coordinate specifying assistance screen in the first embodiment of the present invention and for showing an example of displaying a wafer map and an input portion through which an inspection image acquisition condition is inputted.

A first embodiment of the present invention will be explained with reference to FIG. 2 to FIG. 7B. FIG. 2 is a diagram for explaining one example of a configuration of a defect inspection system; FIG. 3 is a diagram for explaining one example of schematic operation logic of the defect inspection system; FIG. 4 is a diagram for explaining one example of an operation flow of the defect inspection system; FIG. 5 is a diagram for explaining a constituent element of an image DB and one example of a DB producing method in the defect inspection system; FIG. 6 is a diagram for explaining one example of defect information comprising an image including a defect, a reference image, and a defect signal image produced from both images; and FIGS. 7A and 7B are diagrams for explaining a defect-coordinate specifying assistance screen.

As shown in FIG. 2, a defect inspection system 100 according to the present embodiment comprises: an inspection apparatus 1000; a defect signal DB producing system 1100 depending on defects to be detected; a defect signal intensity calculating system 1110, an inspection image DB 1120, and a defect signal DB 1130 included in the defect signal DB producing system 1100; a recipe producing system 1200; and the like, wherein they are connected mutually via a local area network (LAN).

As shown in FIG. 3, in the operation logic of the defect inspection system, a DB associated with an inspection image acquisition condition and having, as constituent elements, an inspection image including a defect and a reference image, is first produced (S11). In the operation, as shown in FIG. 5, there is produced the inspection image DB 1120 which includes, as a constituent element 1127, an inspection image acquisition condition 1121, a defect kind information 1119, a defect inspection image 1122 obtained by imaging the vicinity of defect coordinates 1123, and an inspection image 1126 at coordinates of an adjacent die 1128 corresponding to the defect coordinates 1123. Here, the inspection image acquisition condition 1121 is an item which affects the defect inspection image 1122 among parameters which can be changed on a recipe of the inspection apparatus 1000. Though the defect coordinates 1123 where a defect to be detected 90 is present may be checked in advance, if the inspection apparatus includes a function capable of specifying coordinates in detail using a wafer review screen as shown in FIGS. 7A and 7B, the function may be used.

A defect-generated signal intensity is calculated from the inspection image including a defect and the inspection image including no defect, and a DB including, as a constituent element, the signal intensity associated with the inspection image acquisition condition is produced (S12). Further, a defect signal intensity distribution in an area of inspection image acquisition condition items is displayed (S13). An inspection image acquisition condition is selected on a display screen of the defect signal intensity distribution and reflected on a recipe parameter (S14) to output a new recipe (S15).

In FIG. 4, the inspection apparatus 1000 has a function of outputting the defect inspection image 1122 in the vicinity of the defect coordinates 1123 specified on an inspection recipe and the inspection image 1126 in the vicinity of the coordinates 1128 of the adjacent die corresponding to the defect coordinates 1123, and a function of remotely loading a recipe file produced in the outside and performing inspection.

A producing method of the constituent element 1127 of the inspection image DB 1120 will be explained with reference to FIG. 4. First, parameters which do not contribute to an inspection image acquisition condition, such as a wafer map and an inspection region, are set in the recipe producing system 1200. Next, a set range of the inspection image acquisition conditions is specified. Thereby, the recipe producing system 1200 produces a temporary inspection recipe 1260 in which the inspection image acquisition conditions are changed in the set range.

At this time, in the temporary inspection recipe 1260, the defect coordinates are specified, and setting is made to output the defect inspection image 1122 and the inspection image 1126. The temporary inspection recipe 1260 is remotely loaded by the inspection apparatus 1000 to perform inspection, thereby acquiring the defect inspection image 1122 and the inspection image 1126. The producing of the constituent elements is repeated while changing the inspection image acquisition conditions 1121 within a changeable range on the recipe of the inspection apparatus 1000.

Next, a defect signal intensity 1131 is calculated from the constituent element 1127 of the inspection image DB 1120 by the defect signal intensity calculating system 1110, and the defect signal intensity 1131 and the inspection image acquisition condition 1121 are stored in the defect signal DB 1130 in association with each other via a converting means. The producing procedure of the constituent element of the defect signal DB 1130 is performed repeatedly regarding all the constituent elements in the inspection image DB 1120.

Next, in the defect signal intensity calculating system 1110, a constituent element 1139 having the highest defect signal intensity is selected from the constituent elements in the defect signal DB 1130 via an extracting means and, at that time, a defect signal maximum condition parameter file 1140 reflecting the inspection image acquisition condition 1129 is outputted.

For example, a method for calculating the defect signal intensity 1131 from the constituent element 1127 in the inspection image DB 1120 by the defect signal intensity calculating system 1110 includes subtracting the inspection image 1126 from the defect inspection image 1122 to produce a difference image 1141 and setting, as a defect signal intensity 1131, a value of a pixel having the maximum absolute value on the difference image 1141, as shown in FIG. 6.

Next, in the recipe producing system 1200, prior to outputting of an inspection recipe file, a user sets a parameter contributing to no inspection image acquisition conditions, such as a wafer map or an inspection region, selects the defect signal maximum condition parameter file 1140 for writing at a time of setting of the inspection image acquisition conditions, and properly modifies and determines the set parameter to output a new recipe 1300 after updating the inspection image acquisition condition. The new recipe 1300 is loaded into the inspection apparatus 1000 and used as a new inspection recipe.

Note that, as to the defect signal intensity 1131, a method for using a signal value calculated based on defect detection algorithm which is used when defect detection is determined in the inspection apparatus 1000 may be used. When there are a plurality of options in the defect detection algorithm, the defect signal intensity 1131 may be handled in the same way as the other inspection condition items by calculating the defect signal intensity 1131 for each algorithm. Further, the recipe producing system 1200 may have a function of succeeding and setting a parameter which does not contribute to the inspection image acquisition condition by loading a pre-produced recipe.

Second Embodiment

Figure 8:
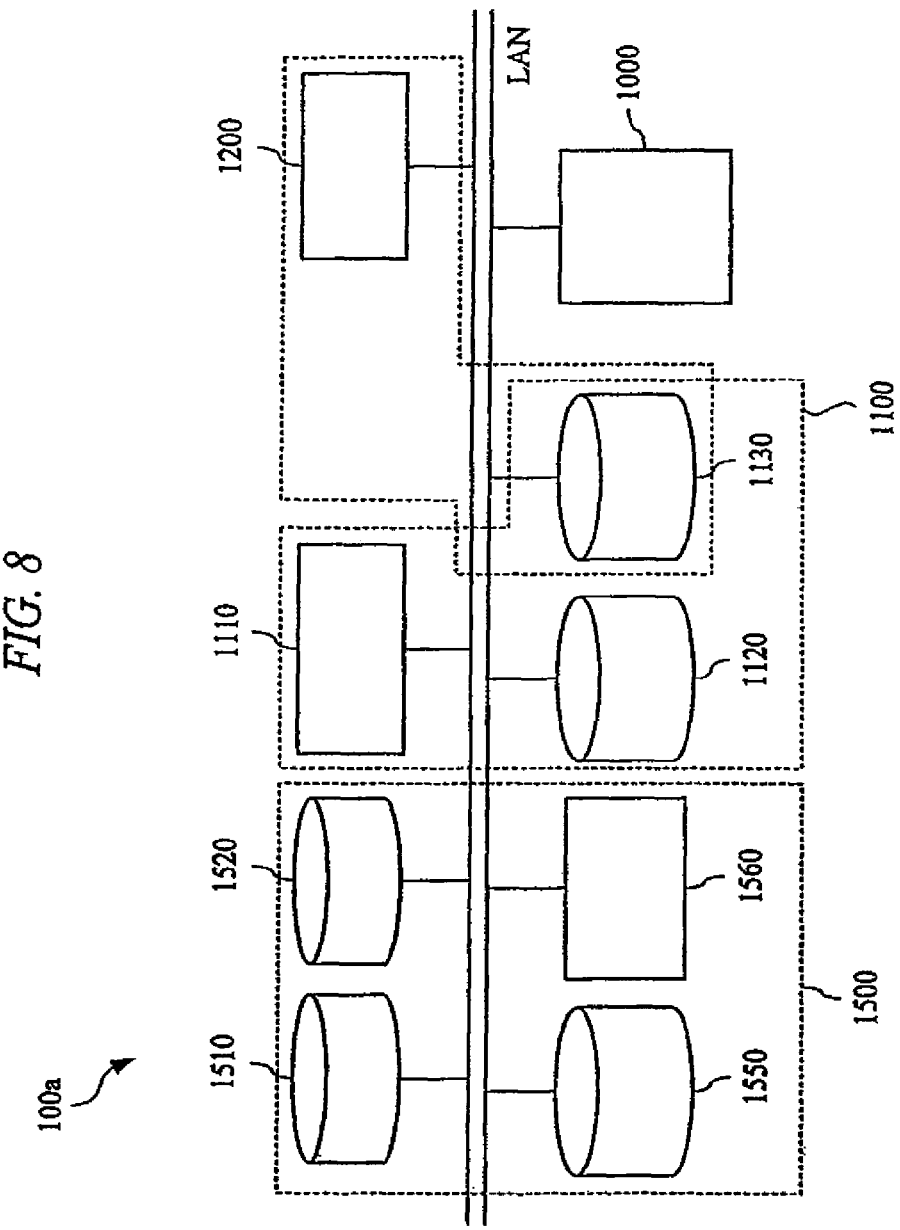
FIG. 8 is a diagram for explaining one example of a configuration of a defect inspection system in a second embodiment of the present invention.
Figure 9:
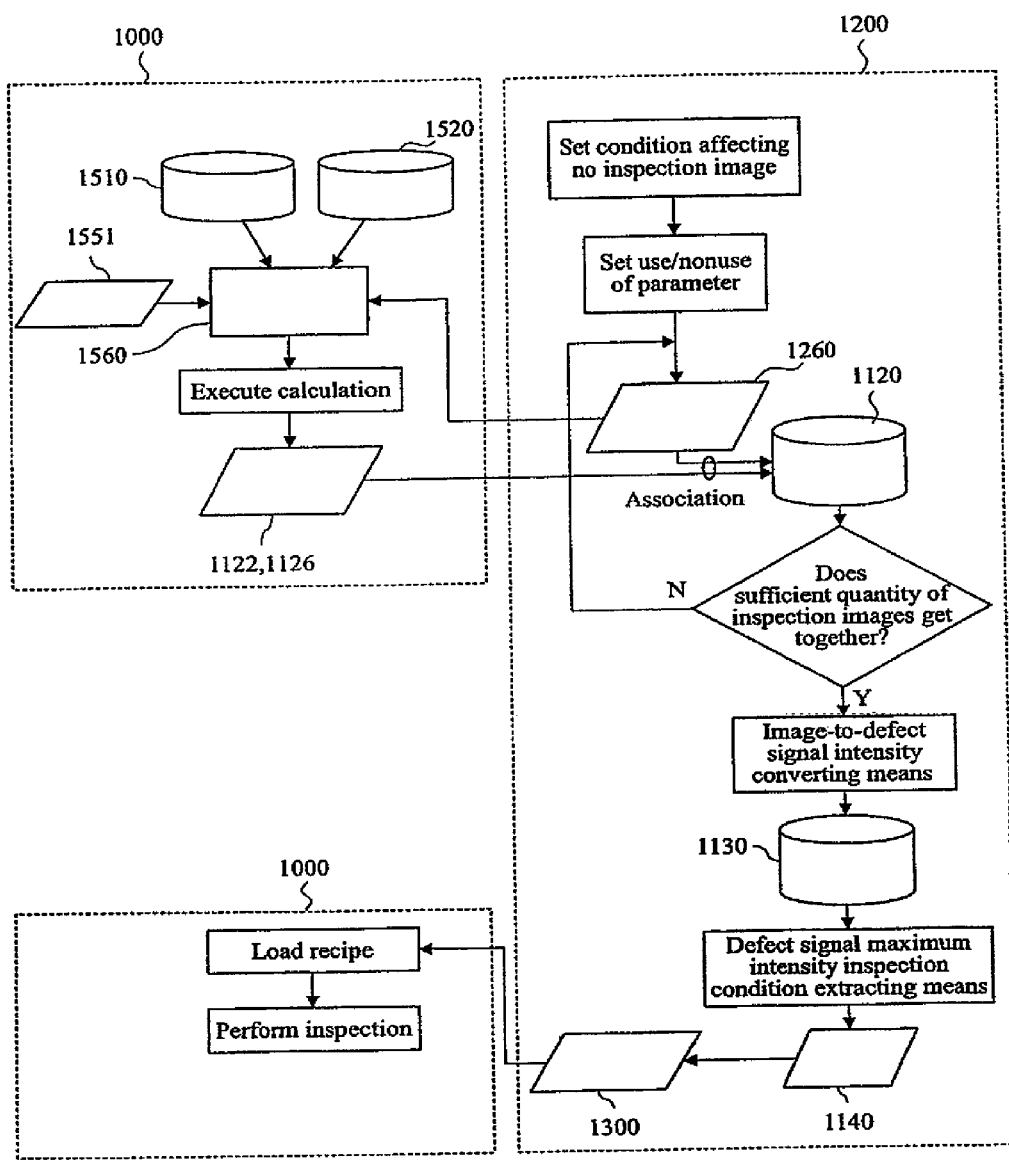
FIG. 9 is a diagram for explaining one example of an operation flow of the defect inspection system in the second embodiment of the present invention.
Figure 10:
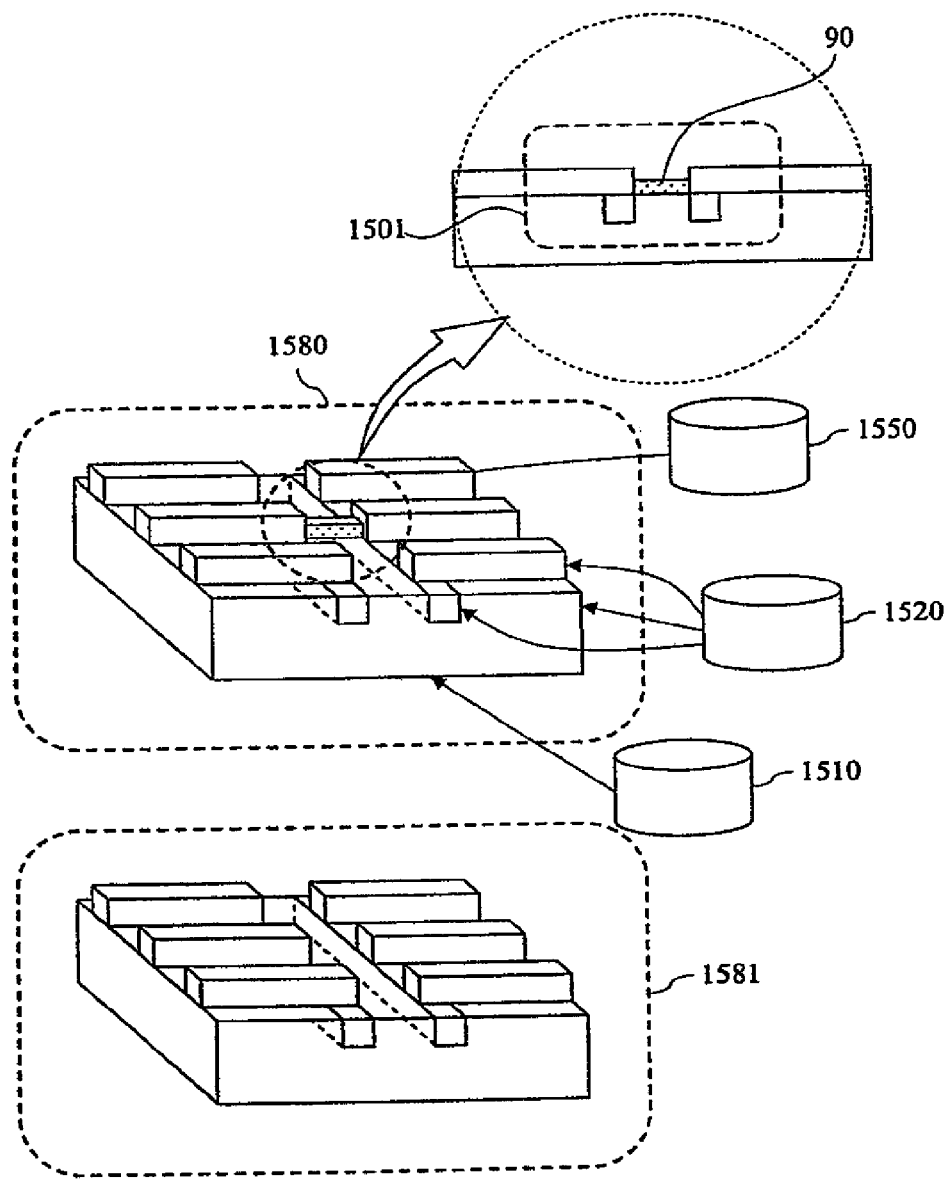
FIG. 10 is a diagram for explaining one example of a simulation model obtained by modeling a defect and its vicinity in the second embodiment of the present invention.

A second embodiment of the present invention will be explained with reference to FIG. 8 to FIG. 10. FIG. 8 is a diagram for explaining one example of a configuration of a defect inspection system; FIG. 9 is a diagram for explaining one example of an operation flow of the defect inspection system; and FIG. 10 is a diagram for explaining one example of a simulation model obtained by modeling a defect and its vicinity.

As shown in FIG. 8, a defect inspection system 100a of the second embodiment comprises: an inspection apparatus 1000; a defect signal DB producing system 1100, a defect signal intensity calculating system 1110, an inspection image DB 1120, and a defect signal DB 1130 included in the defect signal DB producing system 1100; a recipe producing system 1200; an inspection image simulation system 1500; and a structure DB 1510, a material DB 1520, a result DB 1550 for accumulating simulation results, and an inspection image simulator 1560 included in the inspection image simulation system 1500; and the like, whereby they are connected mutually via a local area network (LPN).

Operations of the defect inspection system will be explained with reference to FIG. 9. Prior to the operations of the defect inspection system, as shown in FIG. 10, information 1551 about a defect 90 to be detected is taken out of the result DB 1550 in which simulation results of a process simulator are accumulated, a structure of a sample 1501 in the vicinity of the defect 90 is taken out of the material DB 1510, a constant of a material used in the structure of the sample 1501 is taken out of the structure DB 1520, and a simulation model 1580 of a inspection image including a defect and a simulation model 1581 of an inspection image including no defect are produced from the structure, the material, and the information about the defect.

Next, as shown in FIG. 9, the defect inspection image 1122 and the inspection image 1126, which are the constituent elements 1127 in the inspection image DB 1120, are respectively calculated by the inspection image simulator 1560 using the models 1580 and 1581. Image simulation is repeatedly performed while changing the inspection image acquisition condition 1121.

Next, the defect signal intensity 1131 is calculated from the constituent element 1127 in the inspection image DB 1120 by the defect signal intensity calculating system 1110, and the defect signal intensity 1131 and the inspection image acquisition condition 1121 are stored in the defect signal DB 1130 in association with each other via an image-to-defect signal intensity converting means. The producing procedure of a constituent element in the defect signal DB 1130 is performed repeatedly regarding all the constituent elements of the inspection image DB 1120.

Next, in the defect signal intensity calculating system 1110, the constituent element 1139 having the highest defect signal intensity among the constituent elements in the defect signal DB 1130 is selected via a defect signal maximum intensity inspection condition extracting means, and a defect signal maximum condition parameter file 1140 reflecting the inspection image acquisition condition 1129 is outputted at that time.

For example, a method for calculating the defect signal intensity 1131 from the constituent element 1127 in the inspection image DB 1120 by the defect signal intensity calculating system 1110 includes, like the first embodiment (FIG. 6), subtracting the inspection image 1126 from the defect inspection image 1122 to produce a difference image 1141 and setting, as the defect signal intensity 1131, a value of a pixel having the maximum absolute value on the difference image 1141.

Next, in the recipe producing system 1200, prior to outputting a inspection recipe file, a user sets a parameter contributing to no inspection image acquisition conditions, such as a wafer map or an inspection region, selects the defect signal maximum condition parameter file 1140 for writing at the time of setting the inspection image acquisition condition, and properly modifies and determines a setting parameter to output a new recipe 1300 after updating the inspection image acquisition condition. The new recipe 1300 is loaded into the inspection apparatus 1000 and used as a new inspection recipe.

Note that, as to the defect signal intensity 1131, a method for using a signal value calculated based on defect detection algorithm which is used when defect detection is determined in the inspection apparatus 1000 may be used. When there are a plurality of options in the defect detection algorithm, the defect signal intensity 1131 may be handled in the same way as the other inspection condition items by calculating the defect signal intensity 1131 for each algorithm. Further, the recipe producing system 1200 may have a function of succeeding and setting a parameter which does not contribute to the inspection image acquisition condition by loading a pre-produced recipe.

Third Embodiment

Figure 11:
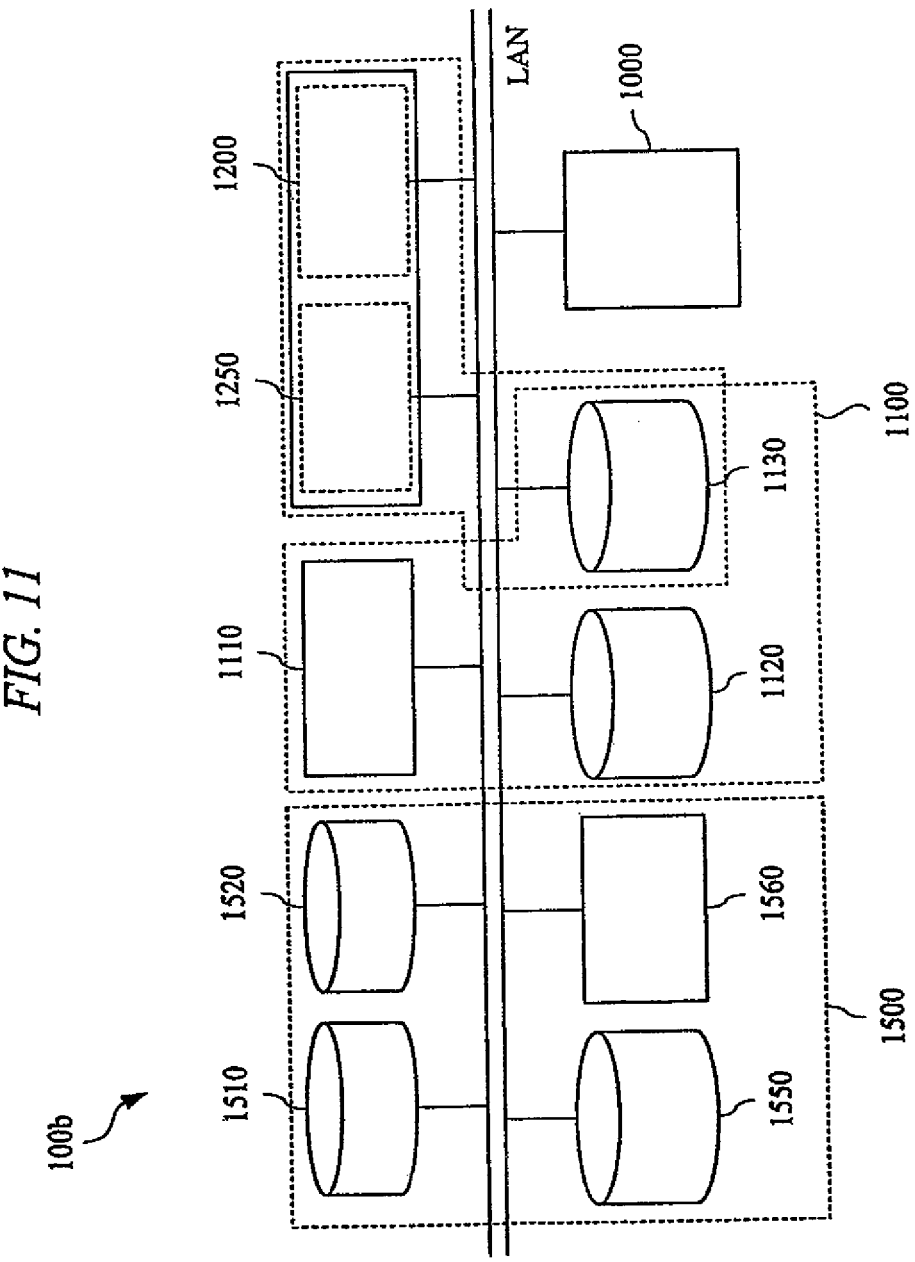
FIG. 11 is a diagram for explaining one example of a constitution of a defect inspection system in a third embodiment of the present invention.
Figure 12:
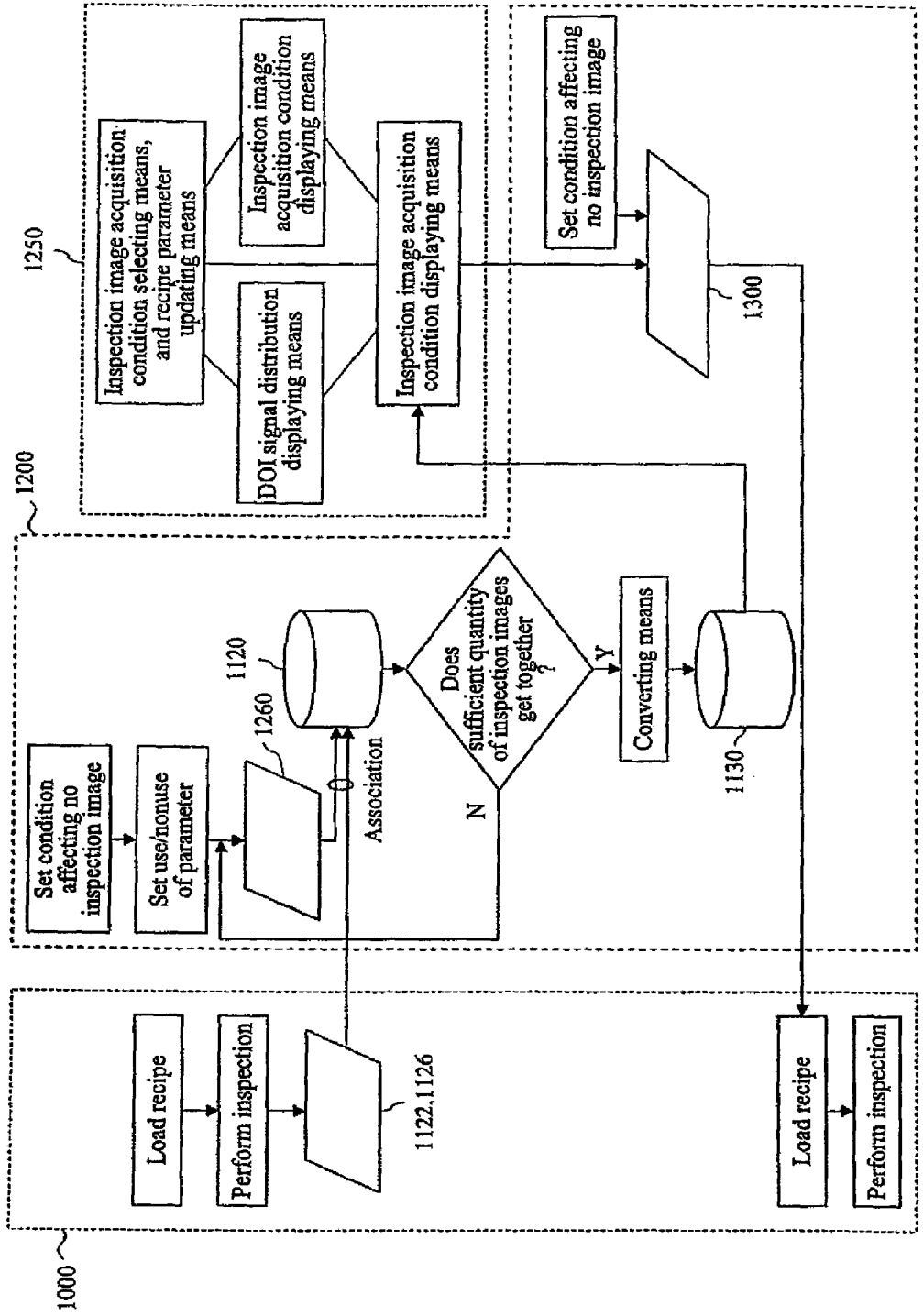
FIG. 12 is a diagram for explaining one example of an operation flow of the defect inspection system in the third embodiment of the present invention.
Figure 13:
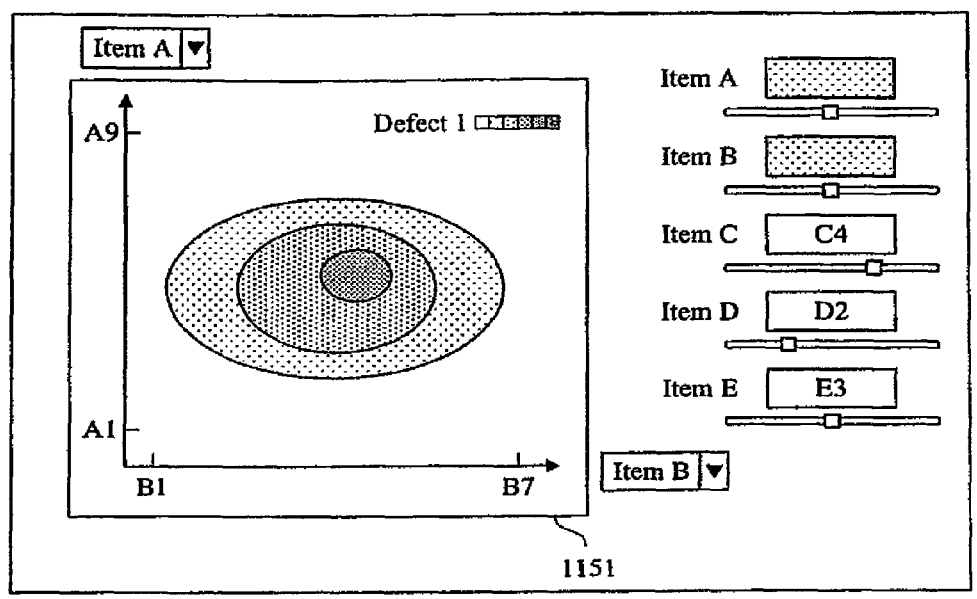
FIG. 13 is a diagram for explaining one example of a display of a defect signal intensity distribution and a user interface concerning the display of the distribution in the third embodiment of the present invention.
Figure 14A:
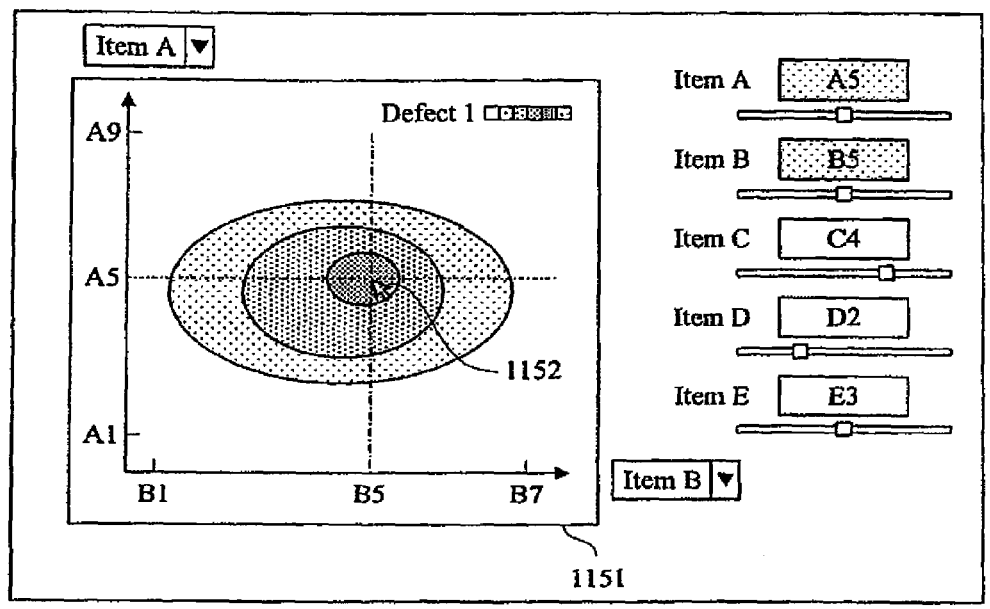
FIG. 14A is a diagram for explaining one example of coordination with a display screen of a defect signal intensity distribution and recipe producing software.
Figure 14B:
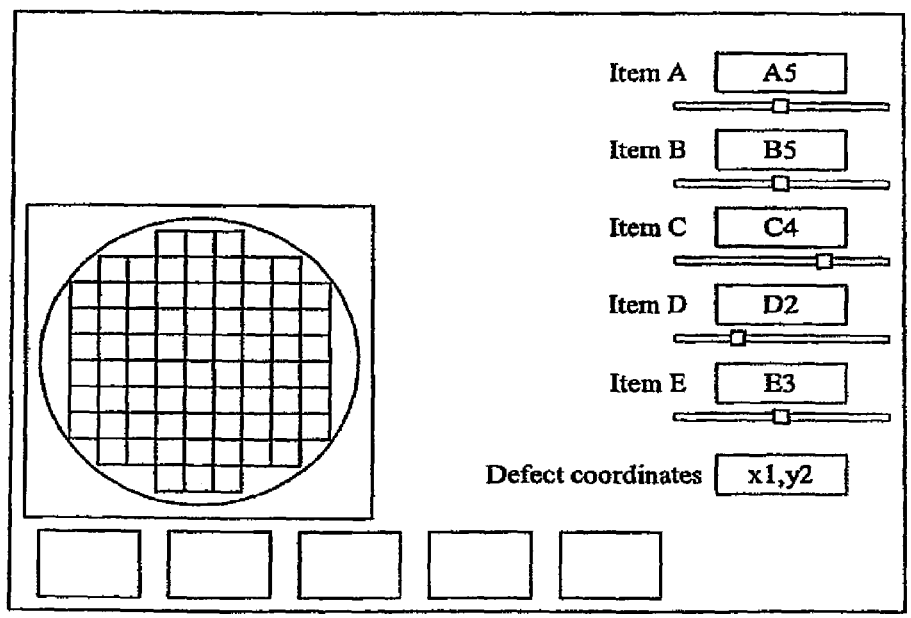
FIG. 14B is a diagram for explaining one example of coordination with a wafer map and the recipe producing software in the third embodiment of the present invention.

A third embodiment of the present invention will be explained with reference to FIG. 11 to FIG. 14B. FIG. 11 is a diagram for explaining one example of a constitution of a defect inspection system; FIG. 12 is a diagram for explaining one example of an operation flow of the inspection system; FIG. 13 is a diagram for explaining one example of display of a defect signal intensity distribution and a user interface concerning the display of the distribution; and FIGS. 14A and 14B are diagrams for explaining one example of coordination with a display screen of a defect signal intensity distribution and recipe producing software.

As shown in FIG. 11, a defect inspection system 100b of the present embodiment includes: an inspection apparatus 1000; a defect signal DB producing system 1100; a defect signal intensity calculating system 1110, an inspection image DB 1120, and a defect signal DB 1130 included in the defect signal DB producing system 1100; a recipe producing system 1200; a defect signal distribution displaying system 1250; an inspection image simulation system 1500; a structure DB 1510, a material DB 1520, a result DB 1550, and an inspection image simulator 1560 included in the inspection image simulation system 1500; and the like, wherein they are connected mutually via a local area network (LAN).

Operations of the defect inspection system will be explained with reference to FIG. 12. The inspection image DB 1120, which is associated with an inspection image acquisition condition 1121, an information about the kind of a defect 1119, a defect inspection image 1122 obtained by imaging the vicinity of defect coordinates 1123, and an inspection image 1126 at coordinates of an adjacent die 1128 corresponding to the defect coordinates 1123 and which is included as a constituent element 1127, is first produced like the first embodiment (FIG. 5).

At this time, the inspection image acquisition condition 1121 is an item affecting the defect inspection image 1122 among parameters capable of changing on a, recipe of the inspection apparatus 1000, and the producing of the above-mentioned constituent element is repeated while changing the inspection image acquisition condition 1121 within a changeable range on the recipe of the inspection apparatus 1000.

Next, a defect signal intensity 1131 is calculated from the constituent element 1127 in the inspection image DB 1120 by the defect signal intensity calculating system 1110, and the defect signal intensity 1131 and the inspection image acquisition condition 1121 are stored in the defect signal DB 1130 in association with each other via a converting means. The producing procedure of the constituent element in the defect signal DB 1130 is performed repeatedly regarding all the constituent elements in the inspection image DB 1120.

For example, the method for calculating the defect signal intensity 1131 from the constituent element 1127 of the inspection image DB 1120 by the defect signal intensity calculating system 1110 may be, like the first embodiment (FIG. 6), a method for subtracting the inspection image 1126 from the defect inspection image 1122 to produce a difference image 1141 and setting, as the defect signal intensity 1131, a value of a pixel having the maximum absolute value on the different image 1141, or a method for using a signal value based on defect detection algorithm which is used when defect detection is determined in the inspection apparatus 1000. At this time, information about a size, a shape, or the like of the defect may be included in the constituent element 1127.

Next, a defect signal intensity distribution map 1151 in an item area of an inspection image acquisition condition as shown in FIG. 13 is displayed using elements of the defect signal DB 1130 via an inspection image acquisition condition displaying means and a DOI signal distribution displaying means. An axis on the display may be set as an item of the inspection image acquisition condition which affects a defect signal intensity most significantly, or be displayed using an axis after axis conversion, or be an arbitrary axis which is selected by a person who produces a recipe. Alternatively, two-dimensional display may be used, or pseudo three-dimensional display may be used.

As shown in FIG. 13, a user interface is provided on the display screen of the defect signal intensity distribution map in order for the person who produces a recipe to arbitrarily select an axis of the graph. A slider for displaying a section in multidimensional space while finely adjusting a parameter may be provided to the user interface.

As shown in FIGS. 14A and 14B, recipe producing software coordinates with software having a function of displaying the defect signal intensity distribution map 1151 in the item area of the above-mentioned inspection image acquisition condition, and places a pointer 1152 such as a mouse on an arbitrary point on the distribution map 1151. Therefore, if the person who produces a recipe executes a position specifying operation such as click operation, a parameter of each item in the inspection image acquisition condition is automatically selected from corresponding coordinates via an inspection image acquisition condition selecting means, so that the inspection condition is reflected on the inspection image acquisition condition on the recipe producing software via a recipe parameter updating means.

Next, in the recipe producing system 1200, a parameter that does not contribute to the inspection image acquisition conditions such as a wafer map or an inspection region is set in advance, and a user properly modifies and determines the set parameter to output a new recipe 1300. The new recipe 1300 is loaded into the inspection apparatus 1000 and used as a new inspection recipe.

Note that although the present embodiment does not clearly indicate a method for acquiring the defect inspection image 1122 and the inspection image 1126 which are the constituent elements 1127 in the inspection image DB 1120, like the above-mentioned first embodiment, the inspection image may be acquired in the inspection apparatus 1000 or calculated by simulation.

Also, the present embodiment does not make any description of the case where any problem occurs at a time of performing inspection using the new recipe 1300 by the inspection apparatus 1000 and anther inspection recipe must be further produced accordingly. However, even in this case, since the inspection image DB 1120 and the defect signal DB 1130 are already present, assistance for producing a recipe becomes possible by immediately displaying the defect signal intensity distribution map 1151, which, needless to say, results in reduction of time for trial and error and in fine adjustment of the inspection condition necessary for producing a recipe.

Fourth Embodiment

Figure 15:
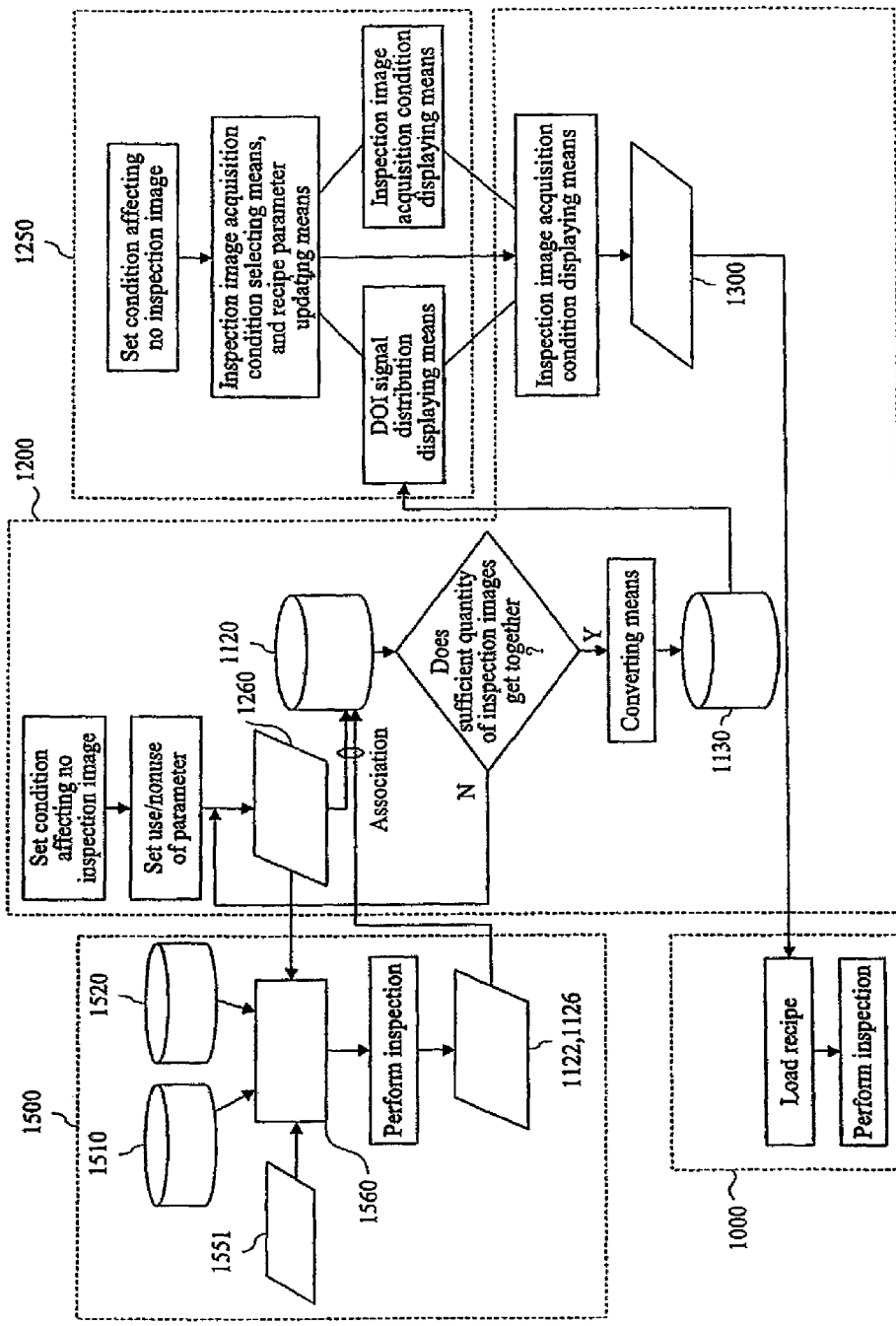
FIG. 15 is a diagram for explaining one example of an operation flow of a defect inspection system in a fourth embodiment of the present invention.
Figure 16:
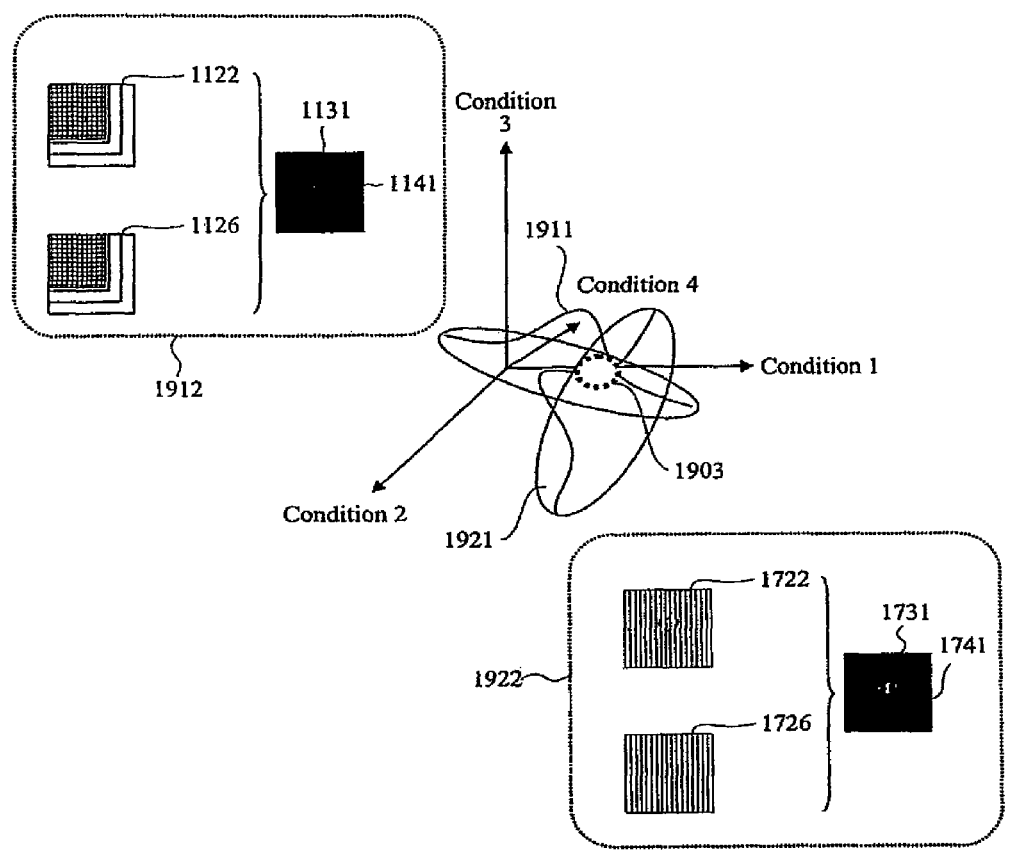
FIG. 16 is a diagram for explaining one example of two kinds of defects, two kinds of images, and a defect signal in the fourth embodiment of the present invention.
Figure 17:
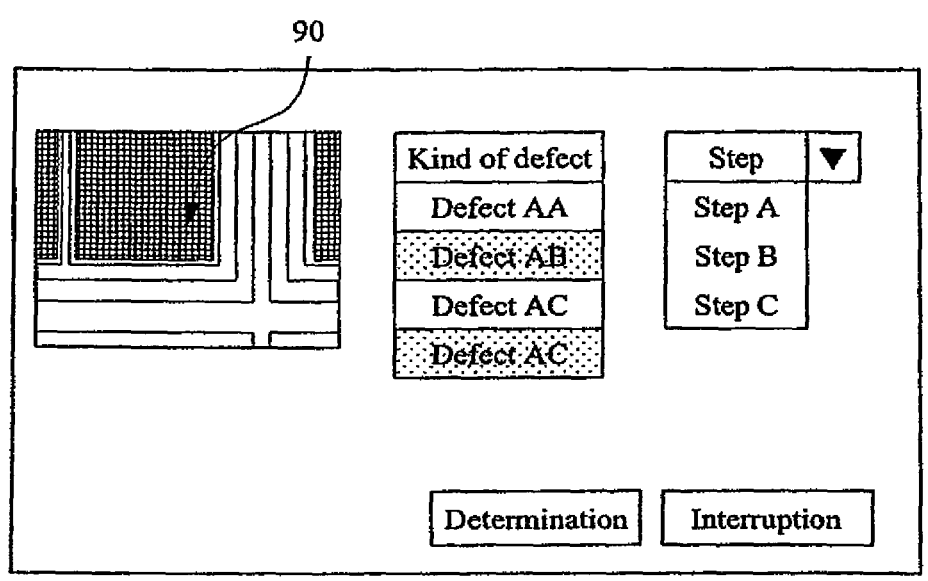
FIG. 17 is a diagram for explaining one example of a user interface for selecting the kind of the defect when a defect signal intensity distribution is displayed in the fourth embodiment of the present invention.
Figure 18A:
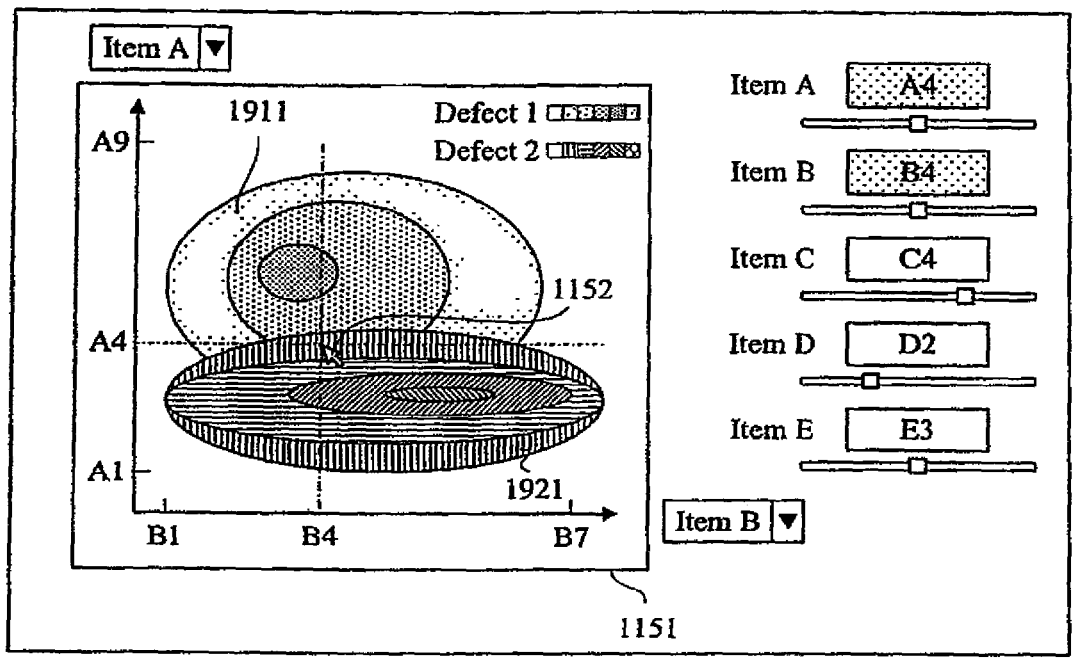
FIG. 18A is a diagram for explaining one example of a user interface for displaying the signal intensity distribution of two kinds of defects in the fourth embodiment of the present invention.
Figure 18B:
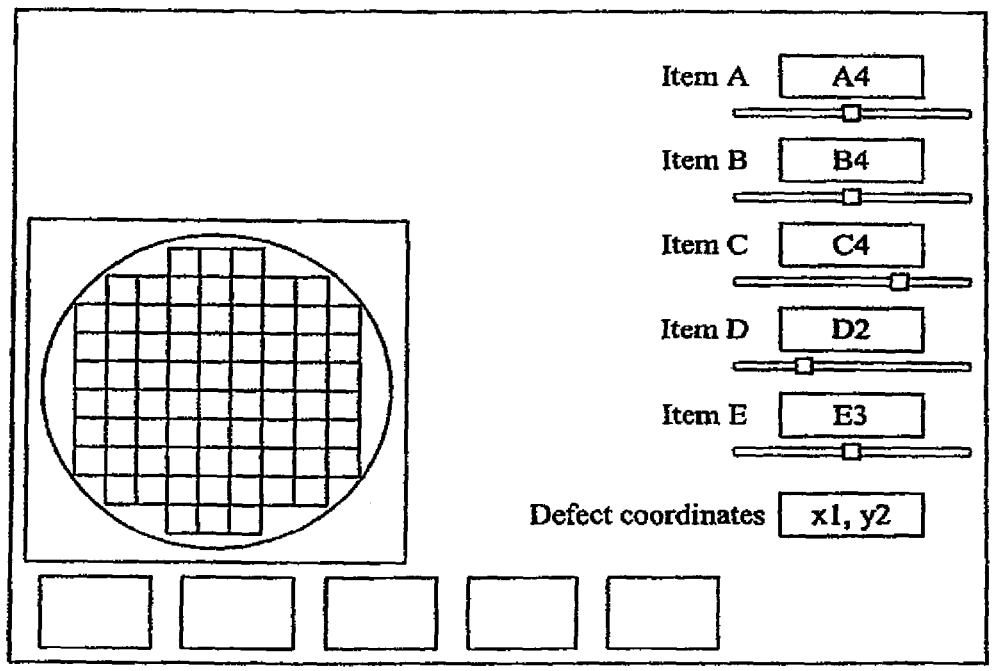
FIG. 18B is a diagram explaining one example of coordination with a wafer map showing a distribution of two kinds of defects on a wafer and with recipe producing software.

A fourth embodiment (modification of the third embodiment) of the present invention will be explained with reference to FIG. 15 to FIG. 18B. FIG. 15 is a diagram for explaining one example of an operation flow of the inspection system; FIG. 16 is a diagram for explaining one example of two kinds of defects, two kinds of images, and a defect signal; FIG. 17 is a diagram for explaining one example of a user interface for selecting a kind of the defect when a defect signal intensity distribution is displayed; and FIGS. 18A and 18B are diagrams for explaining a concept of displaying a signal intensity distribution of two kinds of defects and one example of a user interface associated with the concept.

For example, if an inspection image acquisition condition is set by focusing on a signal intensity of a specific kind of defect when a plurality of defects are present on a wafer processed in one step, it may occur that a signal intensity of another kind of defect becomes low and necessary defect sensitivity cannot be secured. In response to this, there is the case where a recipe must be produced by setting an inspection image acquisition condition for obtaining signal intensities of a plurality of kinds of defects equal to or more than constant values even if signal intensities becomes low in some degree. To such a case, the present embodiment is applied.

Processing procedure for assisting to produce a recipe in operations of the defect inspection system will be explained with reference to FIG. 15. Here, the case of setting an inspection image acquisition condition corresponding to two kinds of defects will be explained.

As to two kinds of defects (a defect 1 and a defect 2), a defect signal intensity relating to the defect 1 and a defect signal intensity relating to the defect 2 are stored together with the information about the kind of a defect 1119 in the defect signal DB 1130 in advance.

An outline of an object of the present embodiment will be explained with reference to FIG. 16. The defect signal intensity 1131 of the defect 1 is calculated using defect information 1912 including a defect inspection image 1122, a reference image (inspection image 1126), and a defect detection signal. The defect signal intensity 1731 of the defect 2 is calculated using defect information 1922 including a defect inspection image 1722, a reference image (inspection image 1726), and a defect detection signal.

In a distribution map in FIG. 16, an example of a defect detection signal intensity distribution 1911 of the defect 1 and a defect detection signal intensity distribution 1921 of the defect 2 when measurement conditions 1 to 4 are changed is simultaneously plotted in a four-dimensional space whose axes are defined by the measurement conditions 1 to 4. When the number of measurement conditions is "n", the distributions 1911 and 1921 are expressed as a distribution in an nth-dimensional space.

The present embodiment provides a means of displaying the defect detection signal intensity distributions 1911 and 1921 on a screen to indicates an effectiveness of overlapping 1903 of both distributions to a person who produces an inspection recipe, thereby providing information for making a determination about whether a signal intensity enough to detect two kinds of defects one time is obtained and providing an interface for selecting such a measurement condition "A" that the person who produces an inspection recipe can obtain sufficiently the signal intensity and for reflecting the same on an inspection recipe.

Next, the person who produces an inspection recipe selects, as shown in FIG. 17, two kinds of defects 90 intended to display the defect signal intensity distributions, namely, the defect 1 and the defect 2 by the defect signal distribution displaying system 1250. Thereby, as shown in FIGS. 18A and 18B, the defect signal intensity distribution map 1151 in which two kinds of defect signal intensity distributions 1911 and 1921 stored in the defect signal DB 1130 are plotted on the same graph is displayed on a screen such as a CRT.

Here, the axis on the display may be set as an item of the inspection image acquisition condition which affects the defect signal intensity most significantly, or be displayed using an axis after axis conversion, or be an arbitrary axis selected by the person who produces a recipe. Alternatively, two-dimensional display may be used, or pseudo three-dimensional display may be used. Also, a user interface for the person who produces a recipe to arbitrarily select an axis of the above graph is provided on the display screen of the above defect signal intensity distribution map.

Like the third embodiment, recipe producing software coordinates with software having a function of displaying the defect signal intensity distribution map 1151 in the item area of the above inspection image acquisition condition, and places a pointer 1152 such as a mouse on an arbitrary point on the above distribution map 1151. Therefore, when the person who produces a recipe performs a position specifying operation such as a click operation, a parameter of each item of an inspection image acquisition condition is automatically selected from corresponding coordinates and the inspection condition is reflected to an inspection image acquisition condition on the recipe producing software.

Subsequently, a new recipe 1300 is outputted by an acceptance/outputting operation from the person who produces a recipe. The new recipe 1300 is loaded into the inspection apparatus 1000 and used as a new inspection recipe.

Note that the present embodiment has described the case where two kinds of defects are present on the same wafer. However, if there is the constituent element 1127 of the inspection image DB 1120 associated with the inspection image acquisition condition 1121, the defect kind information 1119, the defect inspection image 1122 obtained by imaging the vicinity of defect coordinates 1123, and the inspection image 1126 at coordinates of the adjacent die 1128 corresponding to the defect coordinates 1123, then the defect inspection can be performed without limiting the number of kinds of defects to two.

As explained above, according to each embodiment, in condition setting of the defect inspection system for detecting the defect by comparing the inspection image of the object to be inspected and the reference image, the inspection condition setting can be performed easily in a relatively short period of time. It becomes possible to examine the inspection condition setting even when there is no sample. Further, by providing an inspection condition and a defect signal intensity to the person who sets the inspection condition, a function of assisting in the inspection condition setting can be provided.

The invention made by the present inventors is specifically explained based on the embodiments. However, the present invention is not limited to the above-mentioned embodiments and, needless to say, can be variously modified and altered within the scope of not departing from the gist thereof.

The present invention relates to a inspection technique of comparing an inspection image of an object to be inspected obtained by using light, electron beam, or the like and a reference image and of detecting a defect such as a fine pattern defect or a foreign material occurring on a substrate from a difference between the images and, in particular, is effectively applicable to a defect inspection system for performing appearance inspection of a substrate for a semiconductor wafer, a photomask, a liquid crystal, or the like.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A defect inspection method comprising steps of:
   an irradiation step of irradiating light to a sample;
   a detection step of detecting scattered light from the sample which is irradiated in the irradiation step;
   a process step of producing a two dimensional defect signal intensity distribution map having two axes by using a pixel value of a different image between an inspection image and a reference image which is obtained by processing the scattered light detected in the detection step; and
   an inspection-recipe determination step of determining an inspection recipe by using the defect signal intensity distribution map which is produced in the process step,
   wherein both axes of the defect signal intensity distribution map which is produced in the process step are inspection condition items of the inspection recipe which affect the inspection image.

2. The defect inspection method according to claim 1, wherein an item of one of the axis of the defect signal intensity distribution map which is produced in the process step is set.

3. The defect inspection method according to claim 1, wherein the defect inspection method further includes a display step of displaying the defect signal intensity distribution map which is produced in the process step.

4. The defect inspection method according to claim 1, wherein the defect signal intensity distribution map which is displayed in a display step is displayed with a contrast corresponding to a magnitude of a defect signal intensity.

5. The defect inspection method according to claim 1, wherein the defect inspection method further includes a selection step of selecting an arbitral position of the defect signal intensity distribution map which is displayed in a display step and setting a parameter of an inspection recipe for the position selected.

6. The defect inspection method according to claim 1, wherein, in a display step, a plurality of defect signal intensity distribution maps respectively corresponding to a plurality of defects are displayed.

7. The defect inspection method according to claim 1, wherein the defect signal intensity distribution map which is produced in the process step is a plurality of defect signal intensity distribution maps respectively corresponding to a plurality of defects.

8. The defect inspection method according to claim 7, wherein, in the inspection-recipe determination step, an inspection recipe is determined in accordance with a degree of overlapping among the plurality of defect signal intensity distribution maps.

9. A defect inspection apparatus comprising:
an inspection device configured to irradiate light to a sample;
a detector configured to detect scattered light from the sample which is irradiated by the inspection device;
a processor configured to produce a two dimensional defect signal intensity distribution map having two axes by using a pixel value of a different image between an inspection image and a reference image which is obtained by processing the scattered light detected by the detector; and
an inspection-recipe determination device configured to determine an inspection recipe by using the defect signal intensity distribution map which is produced in the processor step,
wherein both axes of the defect signal intensity distribution map which is produced by the processor step are inspection condition items of the inspection recipe which affect the inspection image.

10. The defect inspection apparatus according to claim 9, wherein an item of one of the axis of the defect signal intensity distribution map which is produced by the processor is set.

11. The defect inspection apparatus according to claim 9, wherein the defect inspection apparatus further includes a display device configured to display the defect signal intensity distribution map which is produced by the processor.

12. The defect inspection apparatus according to claim 11, wherein the defect signal intensity distribution map which is displayed by the display device is displayed with a contrast corresponding to a magnitude of a defect signal intensity.

13. The defect inspection apparatus according to claim 11, wherein the defect inspection apparatus further includes a selection device configured to select an arbitral position of the defect signal intensity distribution map which is displayed by the display device and to set a parameter of an inspection recipe for the position selected.

14. The defect inspection apparatus according to claim 9, wherein, in a display device, a plurality of defect signal intensity distribution maps respectively corresponding to a plurality of defects are displayed.

15. The defect inspection apparatus according to claim 9, wherein the defect signal intensity distribution map which is produced by the processor is a plurality of defect signal intensity distribution maps respectively corresponding to a plurality of defects.

16. The defect inspection apparatus according to claim 15, wherein, in the inspection-recipe determination device, an inspection recipe is determined in accordance with a degree of overlapping among the plurality of defect signal intensity distribution maps.

* * * * *